128-24 A AU 337 EX

3/15/88 XR 4,730,614

United States Patent [19]

Lacruche et al.

[11] Patent Number: 4,730,614

[45] Date of Patent: Mar. 15, 1988

[54] DEVICE FOR ADVANCING AN ELECTRODE-HOLDER ELEMENT IN AN APPARATUS GENERATING PULSES FOR THE DESTRUCTION OF TARGETS SUCH AS KIDNEY STONES

[75] Inventors: Bernard Lacruche, Chelles; Jean-Louis Mestas; Dominique Cathignol, both of Lyons, all of France

[73] Assignees: Technomed International, Paris; Institut National de la Sante et de la Recherche Medicale (Inserm), Lyon, both of France

[21] Appl. No.: 872,961

[22] Filed: Jun. 11, 1986

[30] Foreign Application Priority Data

Jan. 31, 1986 [FR] France ................................ 86 01380

Apr. 30, 1986 [FR] France ................................ 86 06318

[51] Int. Cl.[4] ................................ A61B 17/22

[52] U.S. Cl. ................................ 128/328; 128/24 A

[58] Field of Search ................................ 128/24 A, 328

[56] References Cited

U.S. PATENT DOCUMENTS 2,559,227 7/1951 Rieber .

3,725,729 4/1973 McDermott et al. .

4,608,983 9/1986 Muller et al. ........................ 128/328

FOREIGN PATENT DOCUMENTS 0124686 11/1984 European Pat. Off. .

2247195 5/1975 France .

719296 12/1954 United Kingdom .

*Primary Examiner*—Michael H. Thaler

*Attorney, Agent, or Firm*—Schechter, Brucker & Pavane

[57] ABSTRACT

This invention relates to a device for advancing an electrode-holder element in particular mounted on a pulse generating apparatus of the type described in U.S. Pat. No. 2,559,227 to Rieber. This advance device comprises a radially projecting element fast with the rear part of the electrode-holder element and a member for controlling same, the radially projecting element being formed by a toothed wheel of fixed axial position with respect to the insulating support and controlled in rotation by two pistons mounted symmetrically on either side of the wheel to control a rotation in both directions. This device allows a greater precision of the advance of the electrode and an increase in the efficiency of destruction of the targets.

24 Claims, 5 Drawing Figures

DEVICE FOR ADVANCING AN ELECTRODE-HOLDER ELEMENT IN AN APPARATUS GENERATING PULSES FOR THE DESTRUCTION OF TARGETS SUCH AS KIDNEY STONES

The present invention essentially relates to a device for advancing an electrode-holder element and to the use thereof in an apparatus generating pulses for the destruction of targets such as tissues, biliary concretions, kidney stones, etc.

U.S. Pat. No. 2,559,227 to RIEBER discloses an apparatus for generating shock waves of high frequency, comprising a truncated ellipsoidal reflector for reflecting the shock waves, a cavity constituting a chamber for reflecting said shock waves, of the same truncated ellipsoidal shape, one of the two focal points of the ellipsoid being disposed in said chamber opposite the truncated part, said chamber being filled with a liquid for transmitting the shock waves, for example an oil, a shock wave generator device, conventionally comprising two electrodes disposed at least partly inside said chamber, with said two electrodes arranged to generate an electric arc or discharge at said focal point located in said chamber opposite the truncated part, and means for selectively and instantaneously delivering an electric voltage to said two electrodes provoking said electric arc or discharge between said electrodes thus generating said shock waves in said liquid contained in said chamber (cf. FIG. 3 and col. 7, line 51 to col. 9, line 30).

The electrodes are made of highly conductive material such as copper or brass and are mounted on an insulator which is supported as a cantilever with the aid of a connector device so as to adjust the spacing therebetween (cf. col. 4, lines 42 to 53, and col. 8, lines 40 to 47).

French Pat. No. 2 247 195 describes a similar apparatus in which the liquid is constituted by water (page 3, lines 23–24).

When the RIEBER or like apparatus is used, it is observed that the discharge at the electrodes is accompanied by a tearing of metal due to the obtaining of an electric arc provoked by a high potential suddenly applied between the two electrodes, as well as to the associated forces. Such tearing of metal leads to a rapid wear of the electrodes which must be changed about every seven hundred pulses, this constituting a major drawback which radically increases the cost of using the apparatus.

European Pat. No. 124,686 already proposes a device for advancing the electrodes, FIG. 3 including a control member simultaneously controlling a movement of approach or of moving away of the electrodes by rotating the control member in one direction or in the opposite direction (cf. page 9, line 11 to page 10, line 11).

However, the support and electrode-advance structure is relatively complicated and expensive to manufacture.

It is therefore an object of the present invention to solve a new technical problem consisting in furnishing a solution of simple design allowing the use of continuously usable electrodes without reducing the efficiency of destruction of the targets.

It is also a principal object of the present invention to solve the new technical problem consisting in furnishing a solution for advancing electrodes with very high precision, thus concomitantly increasing the efficiency of destruction of the targets.

These new technical problems are solved for the first time by the present invention furnishing a solution at relatively low cost while increasing the number of targets destroyed such as tissues, biliary concretions, kidney stones, etc . . . by improving the precision of positioning.

The present invention thus provides a device for advancing an electrode-holder element, particularly in a pulse generating apparatus comprising a reflector, in particular an ellipsoidal reflector, comprising a cavity for reflecting said pulses towards a target, said electrode-holder element being mounted mobile in an insulating support fixed on the wall of the ellipsoidal reflector, and being formed by a rod disposed in a cylindrical cavity in the insulating support, being mobile in axial translation, characterized in that each assembly formed by the electrode and the electrode-holder element is of identical structure, said two assemblies formed by the electrode and the electrode-holder element being independently mounted in said insulating support, in particular so that the two electrodes are located concurrent at the inner focal point of the ellipsoid, a radially projecting element being provided fast with the rear part of the electrode-holder element and being controlled by a control member.

In this way, the electrodes may in particular be advanced independently inside the ellipsoid as a function of the wear involved by the successive shots.

According to a particular feature of the invention, the electrode-holder element is formed by a rod disposed in a coaxial cylindrical cavity in the insulating support, thus being mobile in translation.

The assemblies of the two electrodes and the two electrode-holder elements advantageously lie in line with each other, i.e. coaxially.

According to a particular embodiment, the radially projecting element, fast with the rear part of the electrode-holder element, is rendered fast with a control member proper, mounted to rotate coaxially with respect to the electrode-holder element and outside the insulating support, with the result that, by rotation of the control member, the electrode-holder element moves axially along the insulating support and provokes a relative displacement of the electrode-holder element with respect to the insulating support.

According to another variant of the invention, the radially projecting element is formed by a wheel provided on its periphery with means for setting the wheel in rotation, said wheel being mounted for rotation by said control member acting on said means for setting said wheel in rotation. Said wheel is preferably adapted to be dismounted with respect to the electrode-holder element.

According to a particular feature, the wheel comprises a central, coaxial through orifice through which the electrode-holder element passes, said electrode-holder element being fast in rotation but mobile in translation with respect to said wheel which is of fixed axial position with respect to the insulating support.

The through orifice in the wheel advantageously presents a non-circular and preferably polygonal section, the electrode-holder element also comprising a part of corresponding outer section at the level of said wheel. The electrode-holder element preferably comprises a threaded part cooperating with a corresponding threaded part of the insulating support, thus forming a screw-nut system of which the screw part is advantageously defined by the threaded part of the rod.

According to a particular embodiment, the said wheel is disposed inside a cavity provided in the insulating support and is mounted on an intermediate part of the electrode-holder element.

According to a presently preferred embodiment, the said means for setting the wheel in rotation are constituted by teeth, and the control member comprises at least one piston mobile in translation in a plane perpendicular to the axis of translation of the electrode-holder element and passing through the plane of said teeth of the wheel in order to be able to act on a tooth. The control member preferably comprises two pistons mounted symmetrically on either side of the wheel to control the wheel in the two directions of rotation, i.e. either to advance the electrode, or to move the electrode back, the wheel in that case comprising two sets of teeth advantageously disposed over the whole circumference of the wheel.

According to another particular feature, the threaded part of the electrode-holder element is located at the rear end of the electrode-holder element, the insulating support is composed of two dismountable parts, a first part constituting the principal part of the insulating support and comprising in particular the cavity in which said wheel is disposed, and a second part serving to obturate the cavity comprising a threaded orifice in which the threaded part of the rear end of the electrode-holder element is received.

The wheel advantageously comprises, at the front, a cylindrical shoulder housed in a countersink in the insulating support, and, at the rear, a means for maintaining the wheel in a fixed axial position, such as a system of circlip or key.

Finally, the electrode is advantageously fixed by an intermediate electrode-holder element fitting for example by a dove-tail fitting system on the electrode-holder element.

The invention naturally also includes the pulse generating apparatus for destroying targets such as tissues, biliary concretions, kidney stones, etc. comprising such a device for advancing the electrode-holder element.

The advance system may advantageously be controlled by a motor controlled by the number of shots fired and/or by the sparking voltage of the electric arc.

The apparatus according to the invention is likewise used under the conditions described by RIEBER in U.S. Pat. No. 2,559,227 in the medical field, for the destruction of targets such as tissues or biliary concretions, kidney stones, etc. (extracorporal lithotripsy).

The invention will be more readily understood on reading the following description with reference to the accompanying drawings, in which:

FIG. 1 shows a plan view, by the truncated part of the ellipsoidal reflector, disposed vertically as shown in FIG. 3 of U.S. Pat. No. 2,559,227 to RIEBER, but without membrane, in accordance with a first embodiment of the device for advancing an electrode-holder element according to the invention.

Figure 1:
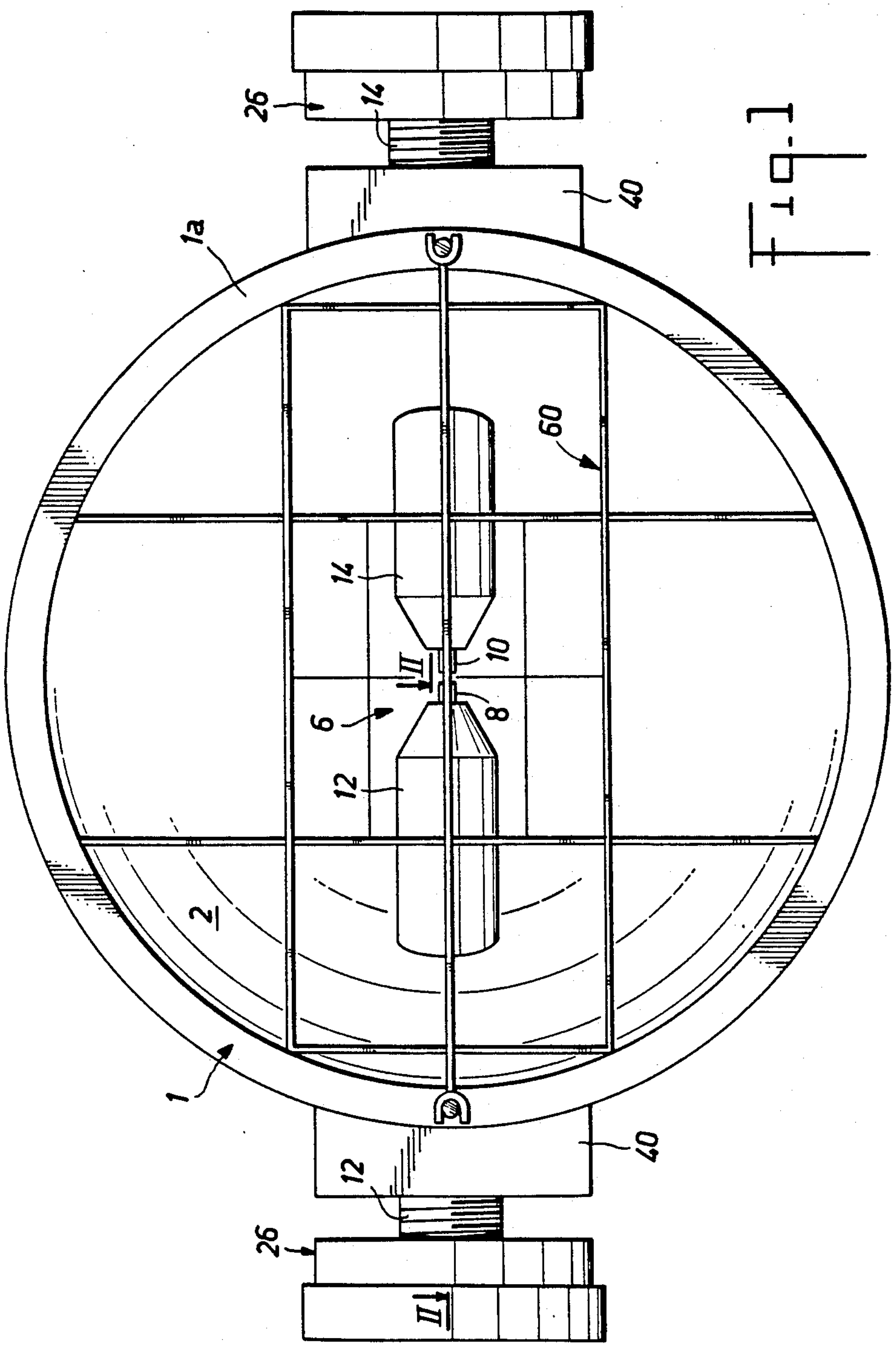
Figure 2:
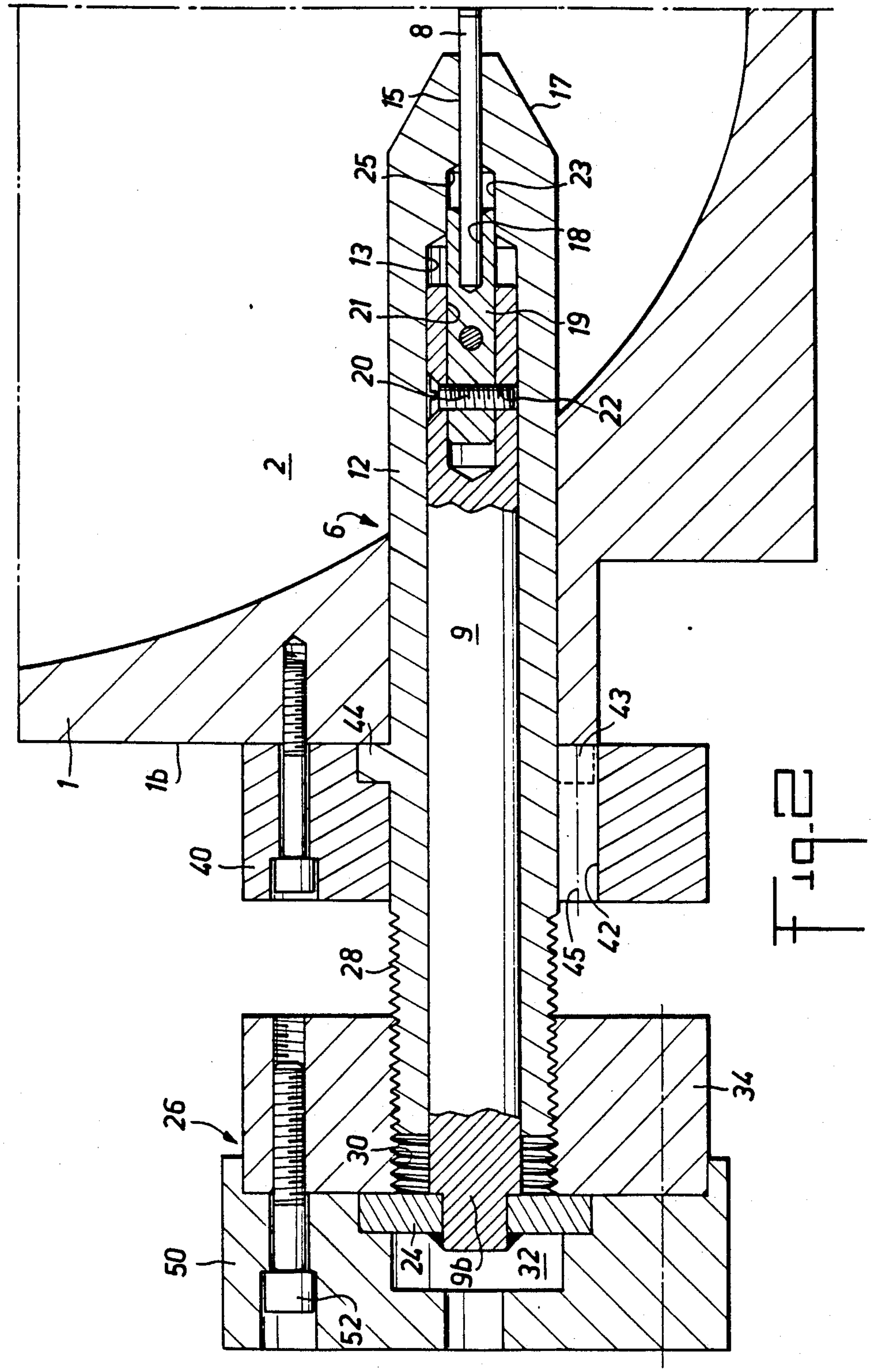
FIG. 2 shows an enlarged view in axial section of the electrode and of the electrode-holder according to the invention, take substantially along line II—II of FIG. 1.

Referring now to the drawings, FIGS. 1 and 2 show an apparatus according to the invention for generating high frequency pulses, of the type generally described by RIEBER in U.S. Pat. No. 2,559,227 with particular reference to FIGS. 1 to 3 thereof. The apparatus according to the invention thus comprises a truncated ellipsoidal reflector disposed vertically, generally referenced 1, for reflecting the pulses, having the shape shown by RIEBER in FIGS. 1 and 3 of U.S. Pat. No. 2,559,227 or the general shape shown in FIG. 3 of French Pat. No. 2 247 195.

This truncated ellipsoidal reflector 1 comprises a cavity 2 constituting a chamber for reflecting the pulses, of the same truncated ellipsoidal shape. Further, one focal point of the two focal points of the ellipsoid 1, is disposed in chamber 2, in its lower part, the other focal point being disposed outside the chamber. A pulse generator device represented by generally at 6, is present and conventionally comprises two electrodes 8, 10. This device 6 is disposed at least in part inside the chamber 2 with the two electrodes 8, 10 arranged to generate an electric discharge or arc at the focal point located in the chamber opposite the truncated part 1*a*. Means (not shown) are provided to deliver, selectively and substantially instantaneously, an electric voltage to the two electrodes 8, 10 providing an electric discharge or arc between the electrodes 8, 10 generating high frequency pulses at the focal point. Electrodes 8, 10 are concurrent at the inner focal point of the truncated ellipsoid.

Means for selectively delivering an electrical voltage to the electrodes, 8, 10 are conventional and described in U.S. Pat. No. 2,559,227 and in French Pat. No. 2 247 195, and generally comprise a source of power delivering a high voltage, generally of the order of 12,000 to 20,000 V, to a capacitor disposed in the electrical circuit connecting the electrodes to the source of power.

According to the present invention, with reference more particularly to FIG. 2, which shows a section along line II—II of FIG. 1, each electrode 8, 10 is connected to an electrode-holder element such as element 9, which is electrically conducting, the assembly formed by each electrode 8, 10 and its electrode-holder element, such as 9, being mounted mobile in an insulating support 12, 14 fixed on the wall of the ellipsoidal reflector.

According to an advantageous feature of the apparatus of the invention, the two electrodes 8, 10 lie in line with each other and are therefore coaxially disposed and symmetrical with respect to the focal point of the ellipsoidal reflector located in chamber 2, opposite the truncated part 1*a* of the ellipsoid.

According to the preferred embodiment shown, the electrode-holder element, such as element 9, FIG. 2, is formed by a rod disposed in a cavity 13 of substantially cylindrical form in the insulating support 12 and coaxial therewith.

In practice, the insulating support 12 therefore also presents the form of a rod which was originally solid and in which a bore defining cavity 13 was made. The front part of the rod forming the insulating support 12 is also pierced and presents an orifice 15 of diameter substantially equal to the diameter of the electrode 8, so as to serve to guide and maintain the electrode. This front part of the insulating support 12 may comprise a bevel 17, as shown. The electrode 8 may be connected by soldering or equivalent means in a housing 18 of an intermediate electrode-holder element constituted by a rod 19. This element 19 is in turn connected in a dismountable manner in an appropriate housing 21 of the electrode-holder element 9, being fixed thereto for example via a screw having its head embedded in the mass of the rod 9. The bore and tapping 20 in the intermediate element 19 and the bore 22 in the electrode-holder element 9, for the passage of the screw, have been shown. A cavity 23 is also provided in the front part of the support 12 of appropriate dimensions to guide the intermediate electrode-holder element 19 and the wall 25 defining one end of cavity 23 serving as a movement stop. The intermediate electrode-holder element 19 is of course made of an electrically conducting material. In certain cases, the electrode-holder element 9 and the intermediate electrode-holder element 19 are made of brass.

According to the invention, the electrodes may be constituted by metals or alloys with a high melting temperature.

According to a particular embodiment, each electrode 8, 10 is made of tungsten, and preferably thoriated tungsten, of which the thorium oxide content is advantageously of the order of 4%.

According to the invention, the rear end 9*b* of the electrode-holder element 9 is provided with a system 26 for advancing the electrode-holder element 9, such as a screw-nut system, so as to effect displacement of the electrode-holder element 9 relative to the insulating support 12 which is itself connected to the ellipsoidal reflector 1 by the presence of an intermediate piece 40; displacement of the electrode 8 is thus obtained. The same structure is provided for electrode 10. According to the embodiment shown, this advancing system 26 is made as follows: the rear part 9*b* of the electrode-holder element 9 is provided with a radially projecting element 24, for example formed by a flange, connected to the electrode-holder element 9. The radially projecting element 24 is maintained against a control member 34 by a protecting cover 50 connected to member 34 by any fixing means such as a screw 52. The cover 50 forms part of the advancing system 26 and serves to block element 24 on member 34. The control member 34 is mounted to rotate outside and coaxially to the insulating support 12, and outside the ellipsoidal reflector 1, so as to allow movement of the control member 34 relative to the insulating support 12.

An appropriate thread 28 may be provided outside the insulating support 12 with a cooperating counter-thread 30 in an orifice provided in the control member 34 which extends as a cavity 32 in a rear part constituting a removable cover 50. The control member 34 is, in fact, in the form of a nut. It will be readily appreciated that, by rotating the advancing system 26, a relative displacement is obtained by coaxial translation of the control member 34 with respect to the insulating support 12 and thus a movement of translation of the electrode-holder 9 and therefore of electrode 8.

The intermediate piece 40 is fixed on ellipsoid 1 in dismountable manner, for example by screws. Piece 12 comprises a radially projecting shoulder 44 clamped against an outer plane wall 1*b* of the ellipsoid 1 by piece 40, so as to block the insulating support 12, by preventing an axial translation thereof along the axis of symmetry of the assembly. A key 45 is housed in a cavity 42 in piece 40 and in an orifice 43 in shoulder 44.

The structure relative to the other electrode 10 is identical.

In order to render replacement of electrodes 8, 10 easy, the cover 50 is provided to be dismountable relative to the control member 34. Thus, to change the electrodes 8, 10, it suffices to dismount the cover 50. The cover 50, once removed, releases the element 24 fast as 9*b* with electrode-holder 9; and the electrode-holder 9 is withdrawn so as to have access to electrode 8 and to its electrode-holder element 19. Only electrode holder element 19 and the electrode are replaced. The same applies to the other electrode 10 and the electrode holder element associated therewith. It will thus be understood that it is possible to adjust the position of electrodes 8 and 10 as desired and that it is therefore possible to make an advance by axial translation of the electrodes inside the ellipsoidal reflector 1 as a function of the wear involved by successive shots.

This progressive penetration of the electrodes may of course be rendered automatic by ensuring the control of the control member 26 by an automatic control device, for example comprising a motor controlled by the number of shots fired and/or by the sparking voltage of the arc. It will be readily understood that the electrodes 8, 10 are connected to the conventional capacitor of the electric circuit via a flexible coaxial cable or the like allowing the displacement in three directions of the firing head formed by the ellipsoidal reflector 1 or semi-ellipsoid.

All the technical advantages described hereinbefore are therefore obtained. The apparatus according to the invention may thus be used in the medical field, particularly for the destruction of tissues, biliary concretions, kidney stones, etc. which have been located at the other focal point of the ellipsoidal reflector 1 as is well known and described in U.S. Pat. No. 2,559,227 and French Pat. No. 2 247 195.

Of course, the invention includes all the means constituting technical equivalents of the means described as well as the various combinations thereof. The dielectric liquid which fills chamber 2 may for example be constituted by water or by an oil, it preferably being constituted by water. The operational conditions will depend on the target to be destroyed, like the potential applied and the frequency and number of electric discharges or arcs generated between electrodes 8 and 10. The sparking electrode may also possibly be provided as described in U.S. Pat. No. 2,559,227. The presence of a membrane forming the chamber of the ellipsoidal reflector containing the liquid is not necessary and this is why it has been eliminated in this invention. The presence of a screen 60 may also be provided, which reduces the electrical leakages in the upper space of the ellipsoid, as described in U.S. copending Application Ser. No. 872,957. The ellipsoidal reflector 1 is preferably made of brass.

Figure 3:
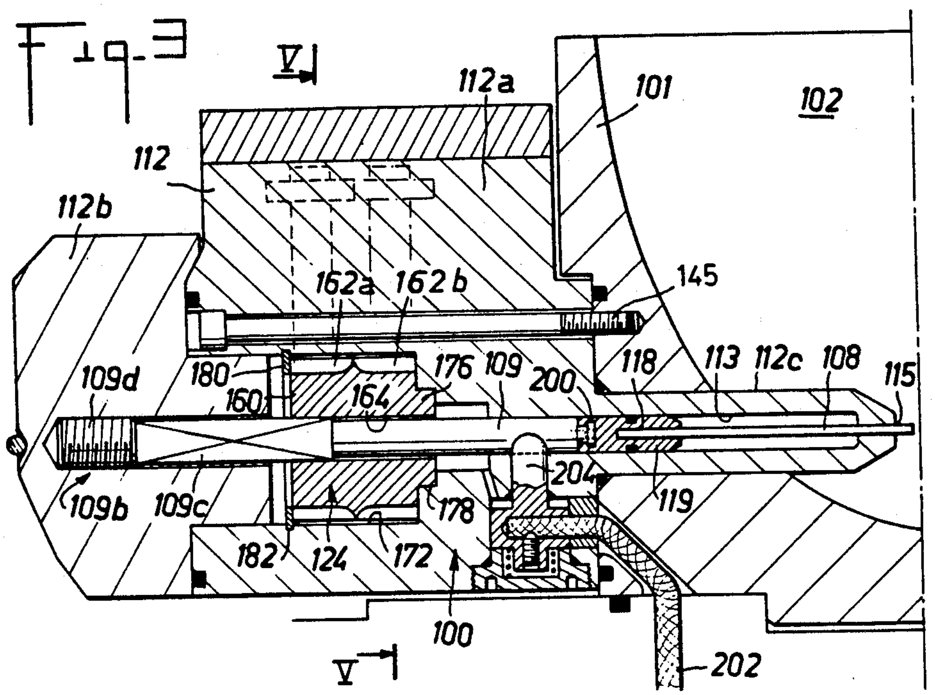
FIG. 3 shows an enlarged view in axial section of a second embodiment of the device for advancing the electrode-holder element according to the invention, as would be seen along the same line II—II of FIG. 1, the electrode-holder element and the electrode being shown in the position most recessed or moved back relative to the ellipsoidal reflector.
Figure 4:
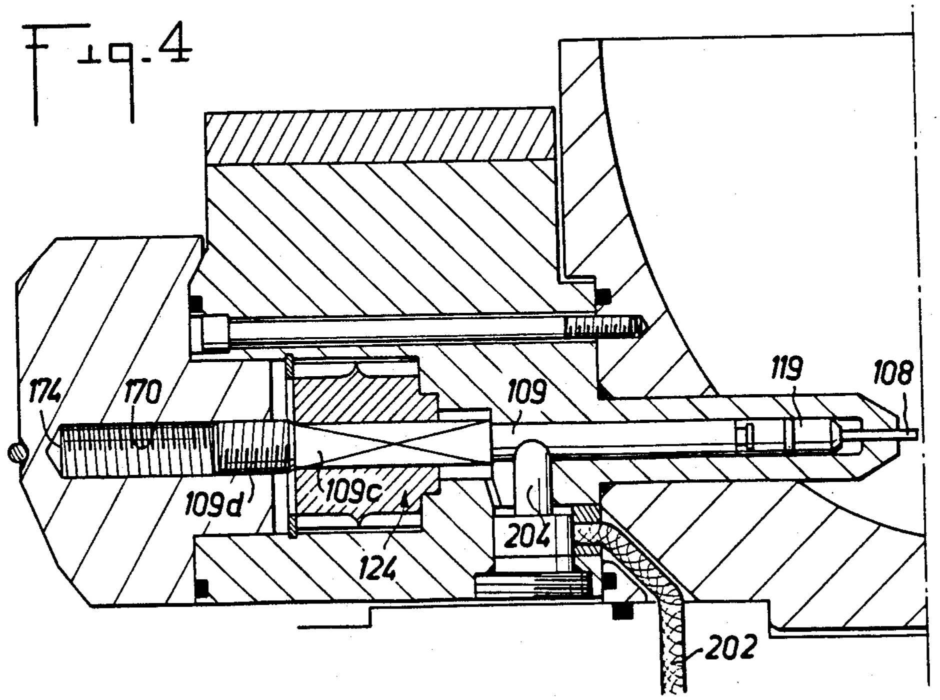
FIG. 4 shows a very advanced position of the electrode-holder element and of the electrode of FIG. 3.
Figure 5:
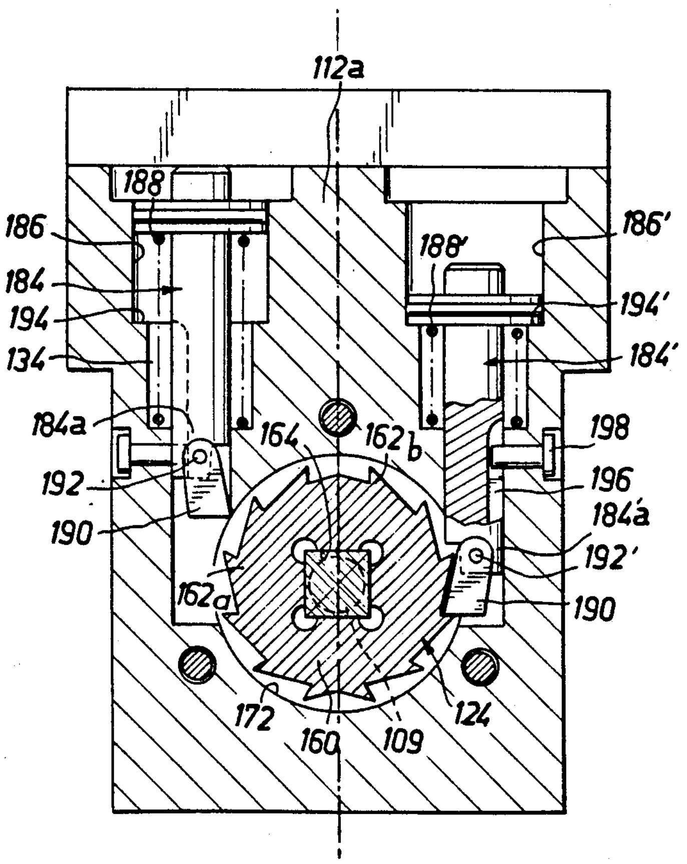
FIG. 5 shows a view in section along line V—V of FIG. 3, showing the teeth on the wheel.

With reference to FIGS. 3 to 5, an advancing device according to the invention, generally referenced 100, is here incorporated in an apparatus generating high frequency shock waves of the type generally described by RIEBER in U.S. Pat. No. 2,559,227, with particular reference to FIGS. 1 to 3. As for the embodiment of FIGS. 1 and 2, this apparatus comprises a truncated ellipsoidal reflector 101 disposed vertically, comprising a cavity 102 constituting a chamber for reflecting the shock waves, of the same truncated ellipsoidal shape.

The detailed description of the ellipsoidal reflector has been indicated with reference to FIGS. 1 and 2.

The advancing device 100 serves to advance an electrode-holder element 109 supporting the electrode 108 proper.

The electrode-holder element 109 is mounted mobile in an insulating support 112 fixed on the wall of the ellipsoidal reflector 101 by appropriate fixing means 145, in a dismountable manner.

The electrode-holder element 109, as described hereinabove, is formed by a rod disposed in a cavity 113 of substantially cylindrical shape, in the insulating support 112, preferably coaxial with respect to the insulating support, being mobile in axial translation.

In practice, the insulating support 112 therefore also presents a front part 112c also in the form of a rod which was originally solid and in which a bore defining the cavity 113 was made. The front part of the rod forming the insulating support 112 is also pierced and presents an orifice 115 of diameter substantially equal to the diameter of the electrode 108, so as to serve to guide and maintain the electrode.

Electrode 108 may be connected by soldering or equivalent means in a housing 118 in an intermediate electrode-holder element likewise constituted by a rod 119.

This intermediate element 119 is in turn connected in dismountable manner to the electrode-holder element 109.

The intermediate electrode-holder element 119 is, of course, made of an electrically conducting material. In certain cases, the electrode-holder element 109 and the intermediate electrode-holder element 119 are made of brass. The electrodes may be made as described with reference to FIGS. 1 and 2.

The device 100 for advancing the electrode-holder element 109 comprises a radially projecting element 124 fast with the rear part 109b of the electrode-holder element 109, and a member 134 for controlling same which is clearly seen in FIG. 5.

According to this embodiment, the radially projecting element 124 is formed by a wheel 160 provided on its periphery with means 162a, 162b for setting the wheel in rotation, said wheel 160 being controlled in rotation by the control member 134 acting on the means 162a, 162b. The wheel 160 is preferably dismountable with respect to the electrode-holder element 109.

The wheel 160 advantageously also comprises a coaxial central through orifice 164 through which the electrode-holder element 109 passes, as is clearly visible in FIGS. 3–5.

The electrode-holder element 109 is fast in rotation with wheel 160 but mobile in translation with respect to wheel 160 which is of fixed axial position with respect to the insulating support 112.

The through orifice 164 of the wheel 160 preferably presents a non-circular, advantageously polygonal section, for example square, as shown in FIG. 5, the electrode-holder element 109 also comprising a part 109c of corresponding outer section, therefore square in the present case, at the level of wheel 160, so as to allow connection in rotation but displacement in translation of the electrode-holder element 109 for an appropriate translation distance.

According to the preferred embodiment shown, the electrode-holder element 109 also comprises a threaded part 109d cooperating with a corresponding threaded part 170 of the insulating support 112, forming a screw-nut system.

According to the embodiment shown, the wheel 160 is disposed inside a second cavity 172 provided in the insulating support 112 and is mounted on the intermediate part 109c of the electrode-holder element.

In the example shown, the threaded part 109d of the electrode-holder element is located at the rear end of said electrode-holder element, and the insulating support 112 is composed of two dismountable parts 112a, 112b respectively. The first part 112a constitutes the principal part of the insulating support and comprises in particular the cavity 172 in which the wheel 160 is disposed and the second part 112b serves to obturate the cavity 172 and comprises a threaded orifice 174 in which is screwed the threaded part 109d of the rear end of the electrode-holder element 109.

The wheel 160 comprises in the front a cylindrical shoulder 176, shown here of reduced section, housed in a countersink 178 in the insulating support 112; and, to the rear, means 180 for maintaining the wheel 160 in fixed axial position, for example a circlip system as shown or a key system, clipping in an annular notch 182 in the wall of the insulating support 112 defining the cavity 172.

According to the preferred embodiment shown, the means 162 for setting the wheel in rotation are constituted by teeth.

In addition, the control member 134 comprises at least one piston 184 mobile in translation in a plane perpendicular to the axis of translation of the electrode-holder element and passing through the plane of said teeth 162 of the wheel 160 in order to be able to act on a tooth, as shown in the right-hand part of FIG. 5.

The control member 134 preferably comprises two pistons 184, 184' mounted symmetrically on either side of the wheel 160 to control the wheel 160 in both directions of rotation, i.e. either to effect a movement of advance of the electrode-holder element and therefore of the electrode, or to move them back. In that case, wheel 160 comprises two sets of teeth 162a–162b disposed over the whole circumference of wheel 160, in opposite directions, preferably each over a half-circumference, as shown.

It will be observed that pistons 184, 184' are also disposed in appropriate housings 186, 186' in the insulating support. These pistons may be controlled by hydraulic control, the piston tending to be repelled against the pressure applied by the hydraulic fluid by the presence of a spring 188, 188' or the like.

It will be observed that the front end 184a, 184a' of each piston 184, 184' is provided with an element 190 forming a pawl mounted to rotate about its respective axis 192, 192' (axis 192, 192' is parallel to the axis of translation of the electrode-holder element 109) so that the plane of rotation of the element 190 is perpendicular to the axis of translation of the electrode-holder element 109.

In addition, the advance movement of the piston is limited by a shoulder 194 of the insulating support 112a. Finally, pistons 184, 184' comprise anti-rotation means constituted by a notch 196 cooperating with a guide lug 198.

It will further be observed that, according to the invention, the intermediate electrode-holder element 119, to which electrode 108 is secured, is fixed by a dove-tail fitting system 200 on the electrode-holder element 109. This allows easy dismantling of the electrode 108 with its intermediate electrode-holder element 119.

The structure of each of the two electrodes is identical, the electrodes being disposed in line with each other as described hereinbefore. Control of each electrode is therefore independent and may be regulated with very high precision.

Electric current arrives from the source of current via a conductor 202 terminating in an electrically conducting element 204 in permanent sliding abutment on the electrode-holder element 109, likewise electrically conducting, in order to provide a sliding electrical contact.

When one of the two pistons, for example piston 184', is hydraulically controlled, it actuates, via its associated pawl 190 a tooth 162 of the wheel 160 through a very small angle of rotation, thus provoking the advance of the electrode-holder element 109 and therefore of electrode 108 over a very short distance.

Very high and very reliable precision is thus obtained of the axial movement of translation of the electrode 108. Control of the pistons may be rendered automatic without difficulty and may be controlled by the number of shots and/or by the sparking voltage of the arc. A system of braking or blocking employing a ball may be provided, in order to block rod 109 and therefore the electrode, in a given position, as a safety measure.

What is claimed is:

1. A device for advancing an electrode-holder element particularly in a pulse generating apparatus comprising a reflector, in particular an ellipsoidal reflector comprising a cavity for reflecting said pulses toward a target, said electrode-holder element being mounted in an insulating support fixed on the wall of the ellipsoidal reflector and being formed by a rod disposed in a cylindrical cavity in the insulating support, said electrode-holder being mounted in said support for axial translation, said electrode-holder element having a front part holding said electrode, an intermediate part and a rear part, said advancing device comprising a wheel means provided on its periphery with rotation means for setting said wheel means in rotation with the aid of a control member acting on said rotation means, wherein said wheel means comprises a central, coaxial through orifice through which one of said intermediate part and said rear part of the electrode-holder element passes, said electrode-holder element being fast in rotation but mobile in axial translation with respect to said wheel means which is of fixed axial position with respect to the insulating support, one of said intermediate part and said rear part of said electrode-holder element comprising axial translation means for producing axial translation of said electrode-holder element as a result of a rotation in either direction of said wheel means by said control member, said electrode-holder element being adapted to be dismounted with respect to said advancing device comprising said wheel means, the rotation means for setting the wheel means in rotation being constituted by teeth, the control member comprising at least one piston mobile in translation in a plane perpendicular to the axis of translation of the electrode-holder element and passing through the plane of said teeth of the wheel means in order to be able to act on a tooth.

2. The device of claim 1, wherein two pistons are mounted symmetrically on either side of the wheel means to control the wheel means in the two directions of rotation, and the wheel means comprises two sets of teeth disposed over the whole circumference of the wheel means.

3. The device of claim 1, wherein said axial translation means comprises a threaded part located at the rear part of the electrode-holder element, and the insulating support is composed of two dismountable parts, and first part constituting the principal part of the insulating support and comprising in particular the second cavity in which said wheel means is disposed, and a second part serving to obturate the second cavity and comprising a threaded orifice in which the threaded part of the rear part of the electrode-holder element is screwed.

4. The device of claim 1, wherein the wheel means comprises, at the front, a cylindrical shoulder housed in a countersink in the insulating support, and at the rear, comprises means for maintaining the wheel in fixed axial position, relative to the insulating support.

5. The device of claim 1, wherein the front end of the piston is provided with an element forming pawl mounted to rotate about an axis parallel to the axis of translation of the electrode-holder element.

6. An apparatus for generating high frequency pulses, comprising a truncated ellipsoidal reflector for reflecting the pulses in the direction of a target, comprising a cavity constituting a chamber for reflecting said pulses of the same truncated ellipsoidal form defining two focal points, one of the focal points of the ellipsoid being disposed in said chamber opposite said truncated part, said chamber being filled with a pulse transmitting liquid, a pulse generating device, conventionally comprising two electrodes, and disposed at least in part inside said chamber, with said two electrodes arranged to generate an electric discharge at the focal point located in said chamber opposite said truncated part; and means for selectively and substantially instantaneously delivering an electric voltage to said two electrodes causing said electrical discharge between said electrodes generating said pulses in said liquid at said focal point, each electrode being connected to an electrically conducting electrode-holder element, the assembly formed by the electrode and the electrode-holder element being mounted for axial translation in an insulating support fixed on the wall of the ellipsoidal reflector, said electrode-holder element having a front part holding said electrode, an intermediate part and a rear part, said electrode-holder element including an advancing device comprising a wheel means provided on its periphery with rotation means for setting said wheel means in rotation with the aid of a control member acting on said rotation means, said wheel means comprising a coaxial central through orifice through which one of said intermediate part and said rear part of the electrode-holder element passes, said electrode-holder element being fast in rotation but mobile in translation with respect to said wheel means which is of fixed position with respect to the insulating support, one of said intermediate part and said rear part of said electrode-holder element comprising axial translation means for producing axial translation of said electrode-holder element as a result of a rotation in either direction of said wheel means by said control member, thereby allowing an adjustment of the electrode position with respect to said focal point located in said chamber, the rotation means for setting the wheel means in rotation being constituted by teeth, the control member comprising at least one piston mobile in translation and in a plane perpendicular to the axis of translation of the electrode-holder element and passing through the plane of said teeth of the wheel means in order to be able to act on a tooth.

7. The apparatus of claim 6, wherein two pistons are mounted symmetrically on either side of the wheel means to control the wheel means in the two directions of rotation, and the wheel means comprises two sets of teeth over the whole circumference of the wheel means.

8. The apparatus of claim 6, wherein the front end of the piston is provided with an element forming pawl mounted to rotate about an axis parallel to the axis of translation of the electrode-holder element.

9. The apparatus of claim 8, further comprising an electrically conducting element in permanent sliding abutment on the electrode-holder element in order to provide a sliding electrical contact.

10. A device for advancing an electrode-holder element in a pulse-generating apparatus comprising an ellipsoidal reflector having a cavity for reflecting said pulses toward a target; said electrode-holder element being mounted for axial translation in an insulating support fixed on the wall of the ellipsoidal reflector, being formed by a rod disposed in a cylindrical cavity in the insulating support, and having a front part holding an electrode, an intermediate part, and a rear part; and said advancing device comprising:

(a) wheel means mounted on the electrode-holder element and being axially fixed relative to the insulating support, the electrode-holder element being rotatably fixed but axially movable relative to said wheel means and the wheel means comprising:
(i) a central, coaxial through orifice through which one of the intermediate and rear parts of the electrode-holder element passes, and
(ii) rotation means provided on its periphery;
(b) a control member acting on said rotation means for rotating the wheel means and the electrode-holder element, the control member comprising means movable in a plane perpendicular to the axis of translation of the electrode-holder element and passing through the plane of said rotation means for engaging and rotating the wheel means and the electrode-holder element; and
(c) axial translation means on one of the intermediate and rear parts of the electrode-holder element for producing axial translation of the electrode-holder element upon rotation of the wheel means by the control member;
said electrode-holder element being adapted to be dismounted with respect to said advancing device.

11. The device of claim 10, wherein the through orifice in the wheel means has a polygonal cross-section, and the electrode-holder element has a corresponding outer section extending through said orifice and abutting said wheel means.

12. The device of claim 10, wherein the wheel means is disposed within a second cavity provided in the insulating support, the wheel means being mounted on said intermediate part of the electrode-holder element.

13. The device of claim 10, further comprising an electrically conducting element in permanent sliding abutment on the electrode-holder element to furnish a sliding electrical contact.

14. The device of claim 10, wherein the wheel means comprises, at its front end, a cylindrical shoulder housed in a countersink in the insulating support and, at its rear end, means for maintaining the wheel means in fixed axial position relative to the insulating support.

15. The device of claim 10, wherein the axial translation means comprises a threaded part cooperating with a corresponding threaded part of the insulating support.

16. An apparatus for generating high frequency pulses and reflecting the pulses in the direction of a target, comprising a truncated ellipsoidal reflector chamber for reflecting the pulses between a pair of focal points, the first of which is disposed within said chamber opposite the truncated portion thereof, said chamber comprising:

(1) a pulse transmitting liquid filling the chamber,
(2) a pulse generating device comprising a pair of electrodes disposed at least in part within the chamber for generating electrical discharges at said first focal point and generating said high frequency pulses in the pulse transmitting liquid thereat,
(3) means for selectively and substantially instantaneously delivering an electric voltage to said electrodes to generate said electrical discharges between said electrodes and produce said pulses,
(4) an insulating support fixed on the wall of the ellipsoidal reflector chamber,
(5) a pair of electrically conducting electrode-holder elements supporting the pair of electrodes, the assembly of each electrode-holder element and the associated electrode being mounted in the insulating support for axial translation relative thereto, and each electrode-holder element having a front part holding the associated electrode, an intermediate part and a rear part, and
(6) an advancing device for axially advancing each electrode-holder element and the associated electrode through the insulating support and into the ellipsoidal reflector chamber to adjust the position of the electrode with respect to said said first focal point, said advancing device comprising:
(a) wheel means mounted on the electrode-holder element and being axially fixed relative to the insulating support, the electrode-holder element being rotatably fixed but axially movable relative to said wheel means and the wheel means comprising:
(i) a central, coaxial through orifice through which one of the intermediate and rear parts of the electrode-holder element passes, and
(ii) rotation means provided on its periphery;
(b) a control member acting on said rotation means for rotating the wheel means and the electrode-holder element, said control member comprising means movable in a plane perpendicular to the axis of translation of the electrode-holder element and passing through the plane of said rotation means for engaging and rotating the wheel means and the electrode-holder element; and
(c) axial translation means on one of the intermediate and rear parts of the electrode-holder element for producing axial translation of the electrode-holder element upon rotation of the wheel means by the control member.

17. The apparatus of claim 16, wherein the through orifice in the wheel means has a polygonal cross-section, and the electrode-holder element has a corresponding outer section extending through said orifice and abutting said wheel means.

18. The apparatus of claim 16, wherein the wheel means is disposed within a second cavity provided in the insulating support, the wheel means being mounted on said intermediate part of the electrode-holder element.

19. The apparatus of claim 16, wherein each assembly formed by the electrode and the electrode-holder element is of identical structure, the two assemblies formed by the pair of electrodes and the associated electrode-holder elements are independent, being independently mounted in said insulating support so that the two electrodes are concurrent at the inner focal point of the truncated ellipsoid.

20. The apparatus of claim 16, wherein the axial translation means comprises a threaded part cooperating with a corresponding threaded part of the insulating support.

21. The apparatus of claim 16, wherein the threaded part of the electrode-holder element lies at the rear end of the electrode-holder element, the insulating support is composed of two dismountable parts, the first part constituting the principal part of the insulating support and comprising a second cavity in which the wheel means is disposed, and a second part serving to obturate the second cavity and comprising a threaded orifice in which the threaded part of the rear end of the electrode-holder element screws.

22. The apparatus of claim 16, further comprising means for automatically controlling the advancing system in response to the number of shots fired and/or by the sparking voltage of the electrical discharge between the electrodes.

23. The apparatus of claim 22, wherein the automatic control device calculates the number of shots fired and actuates the advancing device when a predetermined number is obtained.

24. The apparatus of claim 22, wherein the automatic control device calculates the number of electrical discharges produced between the electrodes and actuates the advancing device when a predetermined number is obtained.

* * * * *